United States Patent
Hsia et al.

(10) Patent No.: US 6,544,553 B1
(45) Date of Patent: Apr. 8, 2003

(54) DOSAGE FORMS AND METHODS FOR ORAL DELIVERY OF PROGESTERONE

(75) Inventors: David Chung Hsia, Irvine, CA (US); Thomas Chun Ho, Irvine, CA (US); Domingo Yap Tan, Irvine, CA (US); Fredric B. Weihmuller, Huntington Beach, CA (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

(21) Appl. No.: 09/473,548

(22) Filed: Dec. 28, 1999

(51) Int. Cl.[7] .............................. A61K 9/20; A61K 9/22; A61K 9/44; A61K 9/46; A61K 9/18
(52) U.S. Cl. .................. 424/465; 424/451; 424/452; 424/457; 424/458; 424/464; 424/468; 424/469; 424/470; 424/489
(58) Field of Search ................................. 424/468, 484, 424/464, 465, 486, 451, 489, 457, 458, 469, 470, 452

(56) References Cited

U.S. PATENT DOCUMENTS

| | | | |
|---|---|---|---|
| 2,032,827 A | | 3/1936 | Andrews |
| 3,432,592 A | | 3/1969 | Speiser .................... 424/19 |
| 4,018,388 A | | 4/1977 | Andrews .................. 241/39 |
| 4,629,621 A | * | 12/1986 | Snipes ..................... 424/19 |
| 4,744,976 A | | 5/1988 | Snipes et al. .............. 424/19 |
| 4,774,074 A | | 9/1988 | Snipes ..................... 424/19 |
| 4,801,460 A | | 1/1989 | Goertz et al. ............. 424/465 |
| 4,806,337 A | | 2/1989 | Snipes et al. .............. 71/65 |
| 5,004,601 A | | 4/1991 | Snipes ..................... 424/78 |
| 5,082,655 A | | 1/1992 | Snipes et al. ............. 424/386 |
| 5,116,619 A | * | 5/1992 | Greco et al. .............. 424/433 |
| 5,140,021 A | * | 8/1992 | Maxson et al. ........... 514/177 |
| 5,518,730 A | * | 5/1996 | Fuisz ...................... 424/426 |
| 5,543,150 A | | 8/1996 | Bologna et al. ........... 424/430 |
| 5,877,216 A | * | 3/1999 | Place et al. ............... 514/573 |
| 6,077,531 A | * | 6/2000 | Salin-Drouin ............. 424/451 |
| 6,086,916 A | * | 7/2000 | Agnus et al. .............. 424/464 |
| 6,117,446 A | * | 9/2000 | Place ...................... 424/435 |
| 6,117,450 A | | 9/2000 | Dittgen et al. |

FOREIGN PATENT DOCUMENTS

| | | | |
|---|---|---|---|
| WO | 95/05807 | * | 3/1995 |
| WO | 97/46242 | * | 12/1997 |
| WO | 99/45932 | | 9/1999 |

OTHER PUBLICATIONS

Budavari et al. eds. (1996). *The Merk Index: An Encyclopedia of Chemcials, Drugs, and Biologicals*. 12th Edition, Merck & Co., Inc.: White House Station, NJ., pp. 1335–1336.

Cuff et al. (Jun. 1998). "A Preliminary Evaluation of Injection Molding as a Technology to Produce Tablets," *Pharmaceutical Technol.* Jun. 1998:96–106.

De Lignieres. (1999). "Oral micronized progesterone," *Clin. Ther.* 21(1):41–60.

Gennaro ed. (1995). *Remington: Practice of the Science and Pharmacy*. Nineteenth Edition, Mack Publishing Co.: Easton, P.A., Ch 64 (pp. 1057–1105), 91 pp. 1598–1614), 92 (pp. 1615–1649), 93 (1650–1659), 94 (1660–1675).

*The United States Pharmacopeia: The National Formulary*. (Jan. 1, 1995). United States Pharmacopeial Convention, Inc.: Rockville, MD., 4 pages total (Table of Contents).

* cited by examiner

*Primary Examiner*—Thurman K. Page
*Assistant Examiner*—S. Tran
(74) *Attorney, Agent, or Firm*—Foley & Lardner

(57) ABSTRACT

Provided is an oral dosage form suitable to deliver a combined dosage of progesterone and which upon delivery through the gastrointestinal tract provides a blood concentration of from about 0.1 ng/ml to about 400 ng/ml progesterone; said dosage form comprising a combination that includes (a) a first solid form comprising from about 25 mg to about 500 mg micronized progesterone in a solid polyethylene glycol carrier having an average molecular weight of from about 1000 to 10,000 and constituting at least about 30% of said first solid form; and (b) a second solid form comprising an estrogen.

8 Claims, 1 Drawing Sheet

DOSAGE FORMS AND METHODS FOR ORAL DELIVERY OF PROGESTERONE

FIELD OF THE INVENTION

This invention relates to oral dosage forms of hormones and methods for their delivery to subjects needing hormone therapy.

BACKGROUND OF THE INVENTION

Micronized progesterone formulations have been disclosed in the past Maxson et al., which discloses various progesterone oral formulations where the first major indgredient is micronized progesterone and "[t]he second major component of the present invention is an oil which serves as a vehicle for the micronized progesterone. The composition and properties of the oil employed as the vehicle have a large effect on the effectiveness of the product." In addition, micronized progesterone has been dissolved or dispersed in a variety of oils to overcome the solubility problem. One commercially available oil-based oral formulation of micronized progesterone is available under the trademark Prometrium®. Salin-Droumn, U.S. Pat. No. 6,077,531, states in its Abstract that it provides "[a] medicament consisting of a biological medium-soluble capsule containing a micronised progesterone suspended in oil is disclosed, characterised in that the capsule also contains estradiol enclosed in microspheres, also suspended in oil, and which consist of one or more polymers that do not dissolve in oil but that dissolve in a biological medium."

In addition to the oil based preparations, various oral progesterone formulations have been proposed:

Agnus et al., U.S. Pat. No. 6,086,916, col. 1, line 56–col. 2, line 4, discusses Gram [Novo Nordisk ]WO 95/05807 as "describ[ing] tablets containing progesterone and a polyethylene glycol, as well as an excipient chosen from the group containing starches, starch-containing components, modified starches, celluloses, modified celluloses, pectins and tragacanth. [T]he presence of polyethylene glycol and of the excipient in the tablets results in a favourable effect on the bio-availability of orally administered progesterone. * * * [T]he tablets * * * contain high percentages of excipients." Gram's Abstract states that she provides an oral progeseterone that "may, conveniently, contain a PEG, and a further excipient selected from the group comprising a starch, a cellulose, pecting, and tragacanth." The polyethylene glycols are referred to as "liquid or solid polymers". Page 7, lines 20–22. Examples with progesterone and estradiol include maize starch, lactose, polyethylene glycol 6000, croscarmellose sodium, magnesium stearate and taclum powder.

Agnus '916 itself has an an object progesterone dosage forms that also include "diluents, disintegrating agents, lubricants and binding agents." Col. 2, lines 36–37. "As examples of diluents, mention may be made of starches, polyols and celluloses * * * preferably pregelatinized maize starch, mannitol and microcrystalline cellulose." Id., lines 38–42. Polyvinylpyrrolidone is said to be the preferred binding agent.

Agnus WO 99/45932 is stated in the English abstract to be "concern[ed with] a pharmaceutical based on natural synthesis progesterone and [ ]estradiol in tablet form, [where] its disintegration time is less than 15 minutes, preferably less than 10 minutes, and more preferably less than 5 minutes." The progesterone used in the formulation is micronized (page 8, Tableau 1, first ingredient). The example has a 9:1 weight ratio of hydroxypropylmethylcellulose:polyethylene glycol 600, where the total quantity of this mixture is 2.0 mg per unit vis a vis 14 mg. sodium carboxymethylcellulose (3.20 mg. in two different forms).

Bair, WO 97/46242, Example 3, discloses gelatin capsules containing a powder of micronized progesterone in calcium carbonate. The micronized progesterone:calcium carbonate is in a 1:4 weight ratio that has been "placed in a grinding mill and blended to yield a homogenous powder" (id., lines 26–27); the powder is administered from a gelatin capsule administered five times per day.

Place, U.S. Pat. No. 6,117,446 and several continuing applications based thereon discloses a buccal dosage unit form for active agents, including progesterone and an estrogen; the examples use a polyethylene oxide and carbomer.

Dittgen et al., U.S. Pat. No. 6,117,450 disclose four differing compressed compositions to be jointly used in an oral dosage form. Example 1 delivers progesterone and estradiol in lactose; one of the four compressed compositions also uses hydroxypropylmethylcellulose and all use a polyvinyl propylene.

Polyethylene glycol has long been known as a polymer matrix for delivery of a wide variety of drugs. Snipes, U.S. Pat. No. 4,629,621, seeks to improve the use of polyethylene glycol by teaming it with an "erosion rate modifier [which] is an insoluble amphiphile * * *, which slows down the rate at which the matrix is eroded * * *." Col. 3, lines 16–23. Examples given are "C12–C20 fatty acids * * *, C12–C20 alcohols * * *, amphiphilic esters of fatty acids with glycerol * * *, C12–C20 amines * * *, and amides of C12–C20 fatty acids. Col. 4, lines 1–10."

SUMMARY OF THE INVENTION

In a first embodiment, there is provided an oral dosage form suitable to deliver a combined dosage of progesterone and which upon delivery through the gastrointestinal tract provides a blood concentration of from about 0.1 ng/ml to about 400 ng/ml progesterone; said dosage form comprising a combination that includes (a) a first solid form comprising from about 25 mg to about 500 mg micronized progesterone in a solid polyethylene glycol carrier having an average molecular weight of from about 1000 to 10,000 and constituting at least about 30% of said first solid form; and (b) a second solid form comprising an estrogen. In one embodiment, the polyethylene glycol carrier comprises from about 45% to about 65% weight of the first solid form. In a further embodiment, the second solid form (b) contains from about 0.25 mg to about 5 mg of estradiol.

In a further embodiment, the solid polyethylene glycol carrier comprises a mixture of polyethylene glycol 1450, polyethylene glycol 3350 or polyethylene glycol 8000. In a preferred embodiment there is provided an oral dosage form suitable to deliver a combined dosage of progesterone and an estrogen via the gastrointestinal tract which upon oral administration provides a blood concentration of from about 0.1 ng/ml to about 400 ng/ml progesterone; said dosage form comprising a combination that includes (a) a first solid form containing from about 25 mg to about 500 mg micronized progesterone, said caplet having been derived from the extrusion of a polymer matrix extruded from a mixture comprising micronized progesterone in a solid polyethylene glycol carrier which is a mixture of polyethylene glycol 1450, polyethylene glycol 3350 or polyethylene glycol 8000, the micronized progesterone having first been dispersed in molten cooling to a solid form, having extruded, said mixture constituting from about 45% to about 65% weight of said first solid form; and (b) a second solid form which contains from about 0.25 mg to about 5 mg of estradiol. In a preferred embodiment, the oral dosage form is provided with said first solid form as a caplet and said second solid form as a tablet.

In a second aspect of the invention, there is provided a method of providing an oral dosage of a combination therapy of progesterone and estradiol which comprises administering to a patient an oral dosage form suitable to deliver a combined dosage of progesterone and an estrogen via the gastrointestinal tract which upon oral administration provides a blood concentration of from about 0.1 ng/ml to about 400 ng/ml progesterone; said dosage form comprising a combination that includes (a) a first solid form containing from about 25 mg to about 500 mg micronized progesterone, said caplet having been derived from the extrusion of a polymer matrix extruded from a mixture comprising micronized progesterone in a solid polyethylene glycol carrier which is a mixture of polyethylene glycol 1450, polyethylene glycol 3350 or polyethylene glycol 8000, the micronized progesterone having first been dispersed in molten polyethylene glycol and, after cooling to a solid form, having been extruded, said mixture constituting from about 45% to about 65% weight of said first solid form; and (b) a second solid form which contains from about 0.25 mg to about 5 mg of estradiol.

The invention features a solid oral dosage form of progesterone comprising a therapeutically effective amount of micronized progesterone and a solid polymeric carrier, wherein the dosage form, upon oral administration, provides a therapeutically effective amount of progesterone to a subject. A preferred solid polymeric carrier is a mixture of polyethylene glycols of molecular weight ranging from about 1,000 to about 10,000. Preferably, progesterone dosage forms of this invention can be prepared by injection molding techniques. Further, the dosage form can be prepared for immediate release or controlled release. The dosage form can be a tablet, capsule, caplet, encapsulated pellets, encapsulated granules, powder, or encapsulated powder. These dosage forms can be provided as unit dosage forms.

The progesterone dosage forms of this invention comprise progesterone from about 25 mg to about 500 mg per dose. The therapeutic serum levels achieved may range from about 0.1 nanogram/ml (ng/ml) to about 400 ng/ml or more. The solid oral dosage forms provide a normalized Cmax of greater than about 0.1 ng/ml/mg. In some aspects, the normalized Cmax may range from about 0.15 ng/ml/mg to about 0.6 ng/ml1mg. In some other aspects, the normalized Cmax may range from about 0.2 ng/ml/mg to about 0.5 ng/ml/mg.

The progesterone dosage forms may also provide a normalized $AUC_{(0-24)}$ greater than about 0.5 ng.hr/ml/mg. In some aspects, the normalized $AUC_{(0-24)}$ may range from about 0.5 ng.hr/ml/mg to about 1.5 ng.hr/ml/mg. In some other aspects, the normalized $AUC_{(0-24)}$ may range from about 0.7 ng.hr/ml/mg to about 1.3 ng.hr/ml/mg. The AUC and other therapeutic levels projected in the application are now superseded by post-filing experimentation that is being made of record in the prosecution history, which provides the more recent experimental data upon which the public should rely. This data is not introduced into the patent specification because of the proscription of entry of new matter under 35 USC § 132.

In some preferred aspects, the polyethylene glycol is polyethylene glycol 1450, polyethylen glycol 3350 or polyethylene glycol 8000, or a mixture thereof.

In some aspects, the cellulose ether is a hydroxyalkyl cellulose, carboxyalkyl cellulose, or a mixture thereof. In some preferred aspects, the cellulose ether is hydroxyethyl cellulose, hydroxypropyl cellulose, carboxymethyl cellulose, carboxyethyl cellulose, hydroxypropylmethyl cellulose, cellulose acetate trimellitate, or a mixture thereof.

In one specific aspect, an oral progesterone unit dosage form is provided which comprises micronized progesterone and a solid polymeric carrier, wherein the dosage form, upon oral administration, provides a therapeutically effective amount of progesterone to a subject, wherein the dosage form comprises from about 25 mg to about 500 mg of micronized progesterone per dose; the solid polymeric carrier constitutes from about 45% to about 65% weight of the dosage form and comprises a mixture of polyethylene glycol 1450, polyethylene glycol 3350 or polyethylene glycol 8000.

In another specific aspect, a combination dosage form is provided which comprises an oral progesterone dosage form and an estrogen dosage form, wherein the combination dosage form is a capsule which encloses the progesterone dosage form and the estrogen dosage form;

the oral progesterone dosage form is a caplet comprising micronized progesterone and a solid polymeric carrier, which progesterone dosage form, upon oral administration, provides a therapeutically effective amount of progesterone to a subject, and the progesterone dosage form comprises from about 25 mg to about 500 mg of micronized progesterone per dose and the solid polymeric carrier constitutes from about 45% to about 65% weight of the progesterone dosage form and comprises a mixture of polyethylene glycol 1450, polyethylene glycol 3350 or polyethylene glycol 8000, and the therapeutically effective amount of progesterone represents a blood concentration of from about 0.1 ng/ml to about 400 ng/ml;

and the oral estrogen dosage form is an estradiol tablet comprising estradiol from about 0.25 mg to about 5 mg of estradiol.

This invention further provides a hormone replacement therapy by administering a dosage form described above to a subject in need of progesterone or a combination of progesterone and estrogen. The method of this invention may be used for treating or preventing various conditions, including, but not limited to, infertility related to non-receptive uterus, premenstrual tension, ovulation, primary dysmenorrhea and endometriosis, habitual abortion, respiratory depression in the Picklwickian syndrome, secondary amenorrhea, dysfunctional uterine bleeding, preeclampsia and toxemia of pregnancy, sexual infantilism, and postmenopausal symptoms.

DETAILED DESCRIPTION OF THE INVENTION

A. General Techniques

Figure 1A:
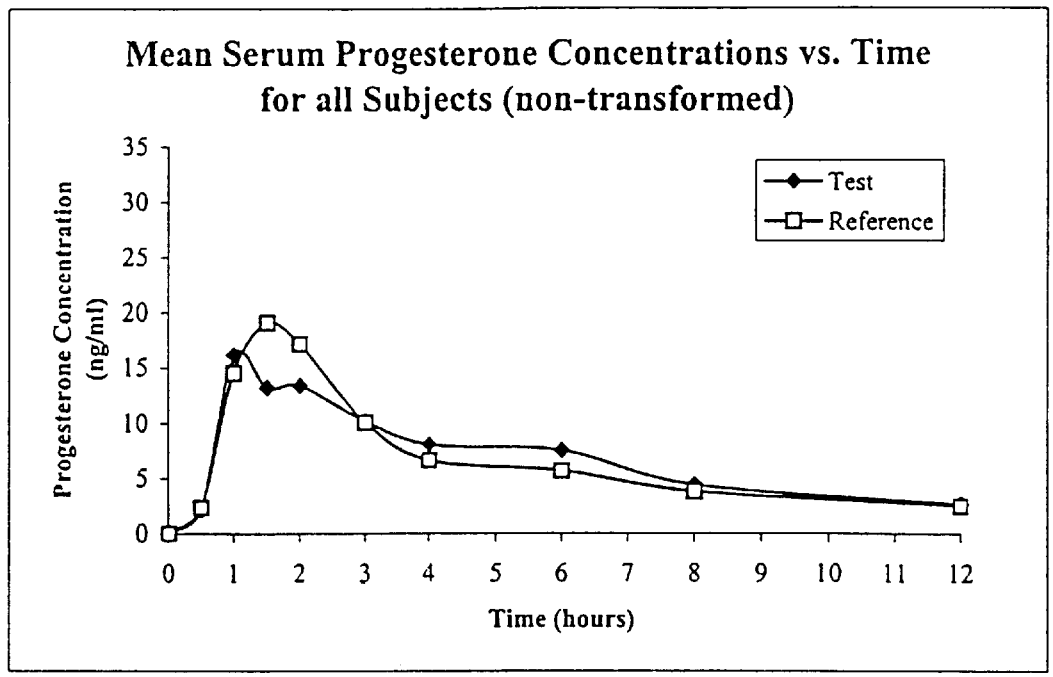
FIG. 1a is a graph showing blood levels of progesterone as a function of time upon oral administration of a progesterone dosage form of this invention.

One of ordinary skill in the art would readily appreciate that the pharmaceutical formulations described herein can be prepared by applying known pharmaceutical manufacturing procedures. Such formulations can be administered to the subject with methods well-known in the pharmaceutical arts. Thus, the practice of the present invention will employ, unless otherwise indicated, conventional techniques of pharmaceutical sciences including pharmaceutical dosage form design, drug development, and pharmacology, as well as of organic chemistry, including polymer chemistry. Accordingly, these techniques are within the capabilities of one of ordinary skill in the art and are explained fully in the literature (See generally, for example, Remington: The Science and Practice of Pharmacy, Nineteenth Edition. Alfonso R. Gennaro (Ed.): Mack Publishing Co., Easton, Pa., (1995), hereinafter REMINGTON, incorporated by reference herein in its entirety).

B. Definitions

As used herein, certain terms may have the following defined meanings.

As used in the specification and claims, the singular forms a, an and the include plural references unless the context clearly dictates otherwise. For example, the term a pharmaceutical may refer to one or more pharmaceuticals for use in the presently disclosed formulations and methods.

The term pharmaceutical generally refers to any known pharmacologically active agent as well as its pharmaceutically acceptable salt, prodrug such as an ester or an ether, or a salt of a prodrug, or a solvate such as ethanolate, or other derivative of such pharmacologically active agent. These salts, prodrugs, salts of prodrugs, solvates and derivatives are well-known in the art.

In addition, this invention contemplates the use of polymorphic, isomeric (including stereoisomeric, geometrically isomeric and optically isomeric) and anomeric forms of the pharmaceuticals described herein.

The terms pharmaceutical and drug as used herein are identical in meaning and thus are used interchangeably.

The term pharmaceutical carrier or simply carrier as used herein refers to a composition that contains and or delivers a pharmacologically active agent and is generally considered to be otherwise pharmacologically inactive.

By solid polymeric carrier is meant a carrier that comprises a polymer or a mixture of polymers that is substantially free of oil. A formulation is substantially free of oil when the formulation does not constitute an oil or a mixture of oils primarily to dissolve or disperse a given drug in the formulation. Inclusion of any combination of polymers or oils which would destroy the solid nature of the said first form is excluded from the scope of the invention.

Formulation is a pharmaceutical term of art that includes a carrier and a pharmaceutical. Formulation is a broad term and includes the compositions that may or may not have been processed into a dosage form which is ultimately administered to a subject. For example, formulation includes the compositions that are mixed in preparation for manufacturing a dosage form.

A dosage form, as used herein refers to a formulation that is ready for administration to a subject. As used herein, it specifically refers to solid dosage forms, including, but not limited to, tablets, capsules, caplets, powders, pellets, and granules. The term also includes multilayered tablets wherein a given layer may represent a different drug. The term also includes powders, pellets and granules that are encapsulated. The powders, pellets, and granules may be coated with a suitable polymer or a conventional coating material to achieve, for example, greater stability in the gastrointestinal tract, or to achieve the desired rate of release. Moreover, the capsule comprising the powder, pellets or granules may be further coated. The tablet, or the caplet may also be scored to facilitate division of dosing. Alternatively, the dosage forms of the present invention may be unit dosage forms wherein the dosage form is intended to deliver one therapeutic dose per administration.

The term pharmaceutically acceptable means that the ingredient that is being qualified is compatible with other ingredients of the formulation and not injurious to the patient. Several pharmaceutically acceptable ingredients are known in the art and official publications. For example, THE UNITED STATES PHARMACOEPIA describe the analytical criteria for assessing the pharmaceutical acceptability of numerous ingredients of interest. Unless otherwise indicated, the ingredients used in the present invention are pharmaceutically acceptable.

Injection molding refers to a process for producing oral solid dosage forms wherein a predetermined amount of the formulation comprising a carrier and a pharmaceutical (along with optional adjuvants) are injected into a mold at a certain temperature and pressure and the mold is cooled and the oral solid dosage form is collected. Optionally, the mold can be packed with additional amount of the formulation material during the cooling cycle. In some aspects, the dosage form is a tablet or a caplet.

A therapeutically effective blood level refers to the blood level of a drug in a subject that is necessary to provide a therapeutic benefit to the subject. The therapeutically effective blood level may vary depending on the therapeutic benefit desired, as well as other variables such as the subject's age, weight, metabolism, physiological conditions such as gastrointestinal motility, renal clearance, etc. The therapeutically effective blood level may be achieved in one or more administrations, applications or dosages. Determination of the dosing needed to achieve a therapeutically effective blood level for a given therapy or treatment is well within the ordinary skill in the pharmaceutical arts.

In the context of hormone replacement therapy, therapeutically effective amount of progesterone is that amount of progesterone effective for one or more of the following, preventing estrogen-induced endometrial hyperplasia in post menopausal women, inducing bleeding in secondary amenorrhea, and reducing endometrial hyperplasia and dysfunctional bleeding in women suffering from such bleeding disorders.

The various therapeutically effective blood levels for various treatments are known in the art. See, for example, de Lignieres, B., Oral Micronized Progesterone, Clin. Ther., 21(1): 41–60 (1999), which is incorporated by reference. The therapeutically effective blood levels may range from about 0.1 ng/ml to about 100 ng/ml or more, depending on the condition being treated and the individual patient-related variables such as age, weight, metabolic activity, etc. See, also for example, the U.S. Pat. No. 5,543,150, which is incorporated by reference, which describes some of the therapeutic serum levels.

The term blood level is used interchangeably with terms such as blood concentration, plasma level, plasma concentration, serum level, serum concentration, serum blood level and serum blood concentration.

Cmax refers to the maximum serum concentration of progesterone following the oral administration of the solid oral dosage form to patients.

Normalized Cmax refers to the value obtained by dividing Cmax into the dosage strength of the solid oral dosage form of progesterone. For example, if the maximum serum concentration of progesterone is 14 ng/ml following the oral administration of a solid oral dosage form containing 200 mg of micronized progesterone, the Cmax is 14 ng/ml and the normalized Cmax is 0.07 ng/ml/mg.

AUC refers to the area under the curve that tracks the serum concentration (ng/ml) of progesterone over a given time following the oral administration of the solid oral dosage form to patients. AUC can be measured from 0 to 12 hours or from o to 24 hrs following the administration and in these cases are referred to as $AUC_{(0-12)}$ or $AUC_{(0-24)}$, respectively.

Normalized AUC is obtained by dividing the AUC into the dosage strength of the solid oral dosage form of progesterone. For example, if the $AUC_{(0-12)}$ is 160 hr.ng/ml following the oral administration of a solid oral dosage form containing 200 mg of micronized progesterone, the normalized $AUC_{(0-12)}$ is 0.8 hr.ng/ml/mg.

The term administration refers to a method of delivering a formulation to a desired site. Specifically, oral administration refers to ingesting a drug by swallowing or chewing.

Subject as used herein refers to a human, both male and female, or an animal (preferably a mammal) that can benefit from the administration of the progesterone formulations of the present invention.

Concentrations, amounts, and other parameters of various components of this invention are often presented in a range format throughout this application. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 0.1 to 100 should be considered to have specifically disclosed subranges such as 0.1 to 1, 0.4 to 10, 1–25, 10–50, 25–60, 40–65, 60–80, 70–100, etc, as well as individual numbers within that range, for example, 0.1, 0.4, 1, 5, 7, 11, 15, 19, 22, 28, 35, 39, 44, 60, 65, 78, 84, 89, 95, etc. This applies regardless of the breadth of the range and regardless of the units under consideration.

C. The Dosage Forms

This invention provides oral progesterone dosage forms comprising micronized progesterone and a solid polymeric carrier, wherein the dosage forms, upon oral administration, provide a therapeutically effective blood level of progesterone to a subject. The currently available oral progesterone dosage forms comprising micronized progesterone are oil-based and thus do not comprise a solid polymeric carrier. The oral dosage forms of the present invention can be processed into an immediate release or a sustained release dosage form. Immediate release dosage forms may release the progesterone in a fairly short time, for example, within a few minutes to within a few hours. Sustained release dosage forms may release the progesterone over a period of several hours, for example, up to 24 hours or longer, if desired. In either case, the delivery can be controlled to be substantially at a certain predetermined rate over the period of delivery.

The oral dosage forms of the present invention can be processed into dosage forms such as tablets, capsules, caplets, powders, encapsulated pellets, encapsulated granules, or encapsulated powders. These dosage forms can be coated with a polymeric or other art-known coating materials to achieve, for example, greater stability on the shelf or in the gastrointestinal tract, or to achieve control over drug release. Such coating techniques and materials used therein are well-known in the art. For example, cellulose acetate phthalate, polyvinyl acetate phthalate, hydroxypropylmethyl cellulose phthalate, methacrylic acid-methacrylic acid ester copolymers, cellulose acetate trimellitate, carboxymethylethyl cellulose, and hydroxypropylmethyl cellulose acetate succinate, among others, can be used to achieve enteric coating. Mixtures of waxes, shellac, zein, ethyl cellulose, acrylic resins, cellulose acetate, silicone elastomers can be used to achieve sustained release coating. See, for example, Remington, supra, Chapter 93, for other types of coatings, techniques and equipment.

Additionally, the tablet or caplet dosage form can be scored to facilitate easy break-off to adjust the dosage as needed. The tablets can also be multi-layered, each layer representing a different drug or a different concentration of the same drug. Alternatively, the dosage forms of the present invention can be prepared as unit dosage forms which are intended to deliver one therapeutically effective dose per administration.

General methods and equipment for preparing tablets, capsules, pellets, and powders are well-known in the art. See, Remington, supra, Chapters 91 and 92.

The present progesterone dosage forms constitute commonly used pharmaceutical excipients to form a stable natural progesterone product without the use of allergenic ingredients such as peanut oil. Further, since the dosage forms of the present invention deliver the natural progesterone, as opposed to synthetic progestins, the undesirable effects of synthetic progestins on liver function and carbohydrate metabolism can be avoided. Additional advantages of these dosage forms include dosing flexibility, convenience, greater patient compliance in a clinical setting and the attendant benefits of improved clinical outcomes.

Various aspects of this invention are described below in greater detail.

a) Progesterone

Progesterone is a steroid hormone secreted primarily from the corpus luteum of the ovary during the latter half of the menstrual cycle. Chemically, progesterone is pregn-4-ene-3,20-dione. Progesterone may exist in two crystalline forms of equal physiologic activity and which are readily interconverted. The α-form is orthorhombic (prisms from dilute alcohol) with a:b:c=0.750:1.0:0.905. These crystals are reported to have a melting point of 127–131° C. The β-form is orthorhombic (needles) with a:b:c=0.563:1.0:0.275. These β-form crystals are reported to have a melting point of 121° C. Merck Index, 12th Edition, pp 1335–1336, Merck & Co., Inc., White House Stattion, N.J. (1996). This invention contemplates using progesterone of either α-form or β-form or a mixture thereof. Accordingly, the term progesterone as used herein refers to either α-form or β-form or a mixture thereof.

The pharmaceutical dosage forms according to the invention constitutes micronized progesterone. Micronized progesterone refers to a white or creamy white crystalline particulated powder that is practically insoluble in water, wherein virtually all (i.e., greater than 90%) of the individual progesterone particles in the powder have been reduced in size to less than about 25 microns in diameter, or in the case of non-round particles, to less than about 25 microns in their largest dimension. In some aspects, virtually all (greater than 90%) of the micronized progesterone particles have particle sizes of less than 10 microns, and a majority (e.g. 78%) of these particles have particle sizes of less than 5 microns.

Micronized progesterone is available from commercial sources such as Berlichem, a division of Schering AG, and from the Upjohn Company. Alternatively, micronized progesterone can be prepared from bulk progesterone in a radiator mill (et air micronizer) by techniques well-known in the art. For a description of the micronization techniques and machines, see, for example, U.S. Pat. Nos. 2,032,827 and 4,018,388.

In a preferred embodiment, the dosage form contains from about 50 mg to about 500 mg progesterone per dose. In another preferred embodiment, the dosage form contains from about 10% to about 70% (more preferably from about 15% to about 60%) by weight of micronized progesterone.

b) The Carrier

The present dosage forms comprise a solid polymeric carrier to deliver micronized progesterone. The solid polymeric carrier may constitute at least 30% by weight of the first solid form that is made up of the micronized progeseterone and solid polymeric carrier.

In even more preferred aspects, the polymeric carrier constitutes from about 30% to about 65% by weight of the first solid form.

The solid polymer in some aspects is a water soluble polymer. Polyethylene glycol is available in various grades under several trademarks including Carbowax® PEG 200, 300, 400, 540 Blend, 900, 1000, 1450, 3350, 4000, 4600, 8000 and compound 20M from Union Carbide Co., USA and Poly Glycols® E series from Dow chemical Co., USA. The various grades available under a given trademarks represent differences in molecular weight and viscosity.

In one aspect, the carrier is a mixture of polyethylene glycols having a molecular weight of from about 100 to about 20,000. In another aspect, the carrier is a mixture of polyethylene glycols having a molecular weight of from about 1000 to about 10,000. In some aspects, the polyethylene glycol is polyethylene glycol 1450, polyethylene glycol 3350 or polyethylene glycol 8000, or a mixture thereof.

It is to be understood that adding additional components to the polymers may be contemplated which is envisioned within the scope of the invention provided there is no deleterious effect on the overall composition and effective therapeutic provision of medication. Thus, in another aspect, the carrier may include a mixture of polyvinylpyrrolidones having a mean molecular weight ranging from 2,500 to 3,000,000 or more. There are many commercially available polyvinylpyrrolidone polymers suitable for the purposes of this invention. In another aspect, the carrier is a cellulose ether. Some exemplary cellulose ethers may include hydroxyalkyl cellulose (such as hydroxyethyl cellulose, hydroxypropyl cellulose, hydroxypropylmethyl cellulose, cellulose acetate trimellitate etc), and carboxyalkyl celluloses (such as carboxymethyl cellulose, carboxyethyl cellulose, etc) or a mixture thereof In some aspects, the carrier may include adjuvants such as opacifiers, bulking agents, sweeteners, stabilizing agents, etc. Examples of opacifiers include titanium dioxide, Talc, calcium carbonate, behenic acid, and cetyl alcohol. Examples of bulking agents include starch, microcrystalline cellulose, calcium sulfate, calcium phosphate, and lactose. Examples of sweeteners include aspartame, saccharin, sodium cyclamate and Xylitol. Examples of stabilizing agents include alginic acid, glycerylmonostearate, hydroxypropyl cellulose, magnesium, aluminium silicate, and propylene glycol.

The above carriers can be used to prepare dosage forms of this invention that can release the progesterone immediately, i.e., within a few minutes to within a few hours, or in a sustained manner, i.e., over a period of 24 hours or longer if desired. The dissolution rate of the progesterone dosage form can be influenced by including adjuvants such as surfactants to the dosage form. Such surfactants may include sodium lauryl sulfate, glyceryl monooleate, sorbitan ester, docusate sodium, and cetrimide. The surfactant may constitute from about 0.1% to about 5% by weight of the dosage form. In one aspect, for example, a polyethylene glycol dosage form of the present invention as described herein may comprise about 2.5% by weight sodium lauryl sulfate to provide an immediate release dosage form.

In the case of sustained release dosage forms, additional solid carriers can be used, including, but not limited to, gums, acrylic resins or a mixture thereof.

c) Combination Dosage Form Comprising Progesterone and an Estrogen

In a further aspect, this invention provides a combination dosage form that comprises an oral progesterone dosage form as described above and an oral estrogen dosage form. Such a combination dosage form can be a tablet, capsule, caplet, powder, encapsulated pellets, encapsulated granules, or encapsulated powder. For example, the combination dosage form can be a capsule which encloses the progesterone dosage form and the estrogen dosage form. The progesterone dosage form and the estrogen dosage form can in turn be independently a tablet, capsule, caplet, powder, encapsulated pellets, encapsulated granules, or encapsulated powder. Alternatively, the progesterone and estrogen can be formulated together into one dosage form such as a powder or a tablet which can be further encapsulated or coated.

Thus, in one aspect, the combination dosage form is a capsule that encapsulates a progesterone tablet and an estrogen tablet. In another aspect, the combination dosage form is a capsule that encapsulates a progesterone tablet and an estrogen powder. The desired dosage form can be chosen depending on the treatment on hand, as well as the desired order of release of the progesterone and the estrogen. For example, by choosing a progesterone caplet and an estrogen powder to prepare a combination capsule, one can achieve a quicker release of estrogen (because the estrogen is a powder) and a slower release of progesterone (because the progesterone caplet requires dissolution first). Selection of the proper dosing and the dosage form for a given treatment is well within the ordinary skill in the art.

Such combination oral dosage forms are feasible because of the development of the oral progesterone dosage forms of the present invention that comprise a solid polymeric carrier. The solid polymeric carrier, unlike the oil-base of the existing dosage forms, allows the production of an oral progesterone dosage form that is of sufficiently small size to facilitate its inclusion, along with an estrogen oral dosage form, in a dosage form such as a capsule to create a dosage form for combination hormone therapy. Thus, a combination of estradiol and progesterone can now be obtained in one oral dosage form by placing, for example, one caplet of progesterone and one tablet of estradiol into a capsule such as a size #1 gelatin capsule.

The estrogen that can be used for the combination dosage form described above can be any one or more of the estrogens that are known in the art. For example, the estrogen can be natural estrogens or their congeners such as estradiol, estrone, estropipate, ethinyl estradiol, quinestrol, or conjugated estrogens. Synthetic estrogens that may be used include dienestrol, diethylstilbestrol, and mestranol. Preferably, the estrogen is estradiol. The estrogen dosage can be from about 0.1 mg to about 10 mg per unit dosage form. The determination of an appropriate dose for a given treatment is within the ordinary skill in the art. For additional details, one may refer to Remington, supra, Chapter 64.

D. Methods of Making a) Injection Molding—A Method of Preparing Progesterone Oral Dosage Forms Comprising Micronized Progesterone and a Solid Polymeric Carrier The oral solid dosage form of progesterone is prepared with a technique known as injection molding. For a general description of this technique, see for example, U.S. Pat. Nos. 3,432,592, 4,801,460, 4,806,337, 5,004,601, and 5,082,655, and Cuff, G. and Raouf, F., Pharmaceutical Technology, 96–106 (1998), all of which are incorporated by reference herein in their entirety.

Briefly, polyethylene glycols are melted and micronized progesterone is dispersed into the molten polyethylene glycol carrier. The micronized progesterone constitutes at least 30% of the mixture. After the dispersion of the progesterone, a small amount of adjuvants such as titanium dioxide (as an opacifier) or pregelatinized starch (as a bulking agent) may be added to the mixture. The melted mixture is cooled down through a lentilling machine to form flakes of lentils. Lentils or even larger sized intermediate flakes can be prepared by melt granulation, lentilling and/or milling. The lentils and the intermediate flakes are passed through a screen of appropriate sieve size to form smaller pieces of lentils. These lentils are made into oral solid dosage forms such as tablets and caplets with techniques known to those skilled in the art, such as injection molding.

During injection molding, a mold is closed and clamped to prevent it from opening. The formulation comprising the pharmaceutical and its carrier is injected into the cavities of the mold through a nozzle. The amount of material that is injected into the mold is controlled by moving a screw to a predetermined distance inside the mold. The screw may be displaced to facilitate packing of additional material into the mold cavities to fill the void generated when the mold cools after the first injection. The various parameters of the injection and packing steps, such as packing time, packing pressure, injection rate, and injection pressure can be adjusted. The mold is cooled and the screw is returned to its pre-injection position. The mold is opened and the molded parts (in this case, the solid unit dosage forms) are ejected. See Cuff and Raouf, supra.

The molded dosage form can be scored with conventional techniques. Alternatively, the mold can be set such that scoring is accomplished through the molding process.

Other techniques known in the art may also be employed to prepare the solid dosage form, including, but not limited to, compression molding, tableting, and extrusion. See, for example, Remington, supra, Chapters 91–94.

b) Combining Progesterone and Estrogen in One Dosage Form

A combination dosage form comprising progesterone and estrogen dosage forms can be prepared by first preparing the progesterone and estrogen formulations or dosage forms separately and then combining them. In one aspect, progesterone and estrogen formulations can be compressed together to form one dosage form, for example, a multilayered tablet wherein each layer represents a progesterone or an estrogen formulation. Alternatively, the progesterone dosage form and the estrogen dosage form can be encapsulated in one capsule. For example, one caplet of progesterone and one tablet of estradiol may be placed into a size #1 hard shell gelatin capsule using an MG encapsulation machine fitted with custom built parts.

Methods of preparing estrogen formulations are well-known in the art. See, Remington, supra, Chapters 91–93. For example, the estrogen formulation can be prepared by direct compression method. In this method, the required quantities of estrogen and a portion of anhydrous lactose are mixed together in a blender. The remaining anhydrous lactose, and, optionally, different types of color aluminum lake, are premixed by passing through a size 20 screen. Other ingredients such as microcrystalline cellulose and polacriline potassium may be added to this mixture. The granulation may be lubricated with magnesium stearate. The granules are then made into tablets on a rotary tabletting machine fitted with appropriate punches and dies to achieve the desired tablet size, thickness, and hardness.

Estrogen may constitute from about 0.5% to about 5% by weight of the tablet, depending on the type of estrogen and the therapeutically effective estrogen blood levels needed for a given treatment. In one example, estradiol constitutes about 1.29% of the weight of the mixture so that a tablet containing 1 mg of estradiol weights about 80 mg and has a diameter of about 7/32 inch. The thickness of a tablet weighing 80 mg is about 0.107 inch.

In one example, the progesterone formulation is a caplet and the estrogen formulation is an estradiol tablet and the combination dosage form is a capsule. Thus, one caplet of progesterone and one tablet of estradiol may be filled into a size #1 capsule using an MG encapsulation machine that is fitted with custom built parts. As described above, individual formulations of progesterone and estrogen can be varied, including, but not limited to, tablets, powders, granules, and pellets. Thus, in other examples, the combination dosage form may be a capsule comprising a progesterone tablet and an estradiol powder.

Different progesterone and estrogen combination formulations have been made possible by the progesterone formulation comprising a solid polymeric carrier. For example, preparation of a combination dosage form with a capsule of standard size 1 is now feasible. A size 1 capsule has an internal diameter of about 0.253 inch and an internal length of about 0.748 inch when fully closed. With the present invention, a progesterone caplet of up to a length of about 0.545 inch and an estradiol tablet of up to a thickness of about 0.115 inch can be placed end to end within a size 1 capsule.

E. Administration

The pharmaceutical dosage forms of this invention can be administered to patients needing hormonal therapy requiring progesterone, either as a replacement or as a supplement. The effective amount of progesterone per dosage form can vary widely, in accordance with the needs of the patient, a dosage of from about 50 to about 500 milligrams per dosage form. The method of administration generally involves swallowing, sucking, or chewing a dosage form of the present invention. Alternatively, the dosage form can be held in the mouth, under the tongue, or next to a cheek for sufficient period such that an effective amount of the progesterone is released from the dosage form. Additional methods of administering oral dosage forms are well known in the art.

The dosage forms of the present invention can be administered to treat or prevent a variety of conditions. Such conditions include infertility related to non-receptive uterus, premenstrual tension, ovulation, primary dysmenorrhea and endometriosis, habitual abortion, respiratory depression in the Pickwickian syndrome, secondary amenorrhea, dysfunctional uterine bleeding, preeclampsia and toxemia of pregnancy, sexual infantilism, and post-menopausal symptoms.

The invention described herein is further illustrated by the following non-limiting examples.

EXAMPLES

Example 1
Progesterone Oral Caplets, 200 mg

The composition for preparing progesterone oral caplets constituting 200 mg of progesterone per caplet is provided in Table 1 below.

TABLE 1

| Component | mg/caplet | % (by weight) |
| --- | --- | --- |
| Micronized progesterone | 200.0 | 43.10 |
| Polyethylene glycol 1450 | 56.6 | 12.20 |
| Polyethylene glycol 3350 | 163.3 | 35.20 |
| Polyethylene glycol 8000 | 41.8 | 9.00 |
| Titanium dioxide | 2.3 | 0.50 |
| TOTAL | 464.0mg | 100.0% |

The required quantities of polyethylene glycol 1450, polyethylene glycol 3350 and polyethylene glycol 8000 were melted into an appropriate size heated kettle. The molten mixture was mixed for 5–10 minutes. Titanium dioxide was passed through a size 20 mesh into the molten mixture and the mixture was stirred for additional 10 minutes. Micronized progesterone was dispersed into the kettle while mixing. After all the micronized progesterone has been added, the mixture was continuously stirred with the turbine speed on for approximately 50 minutes. The material was transferred into a lentilling machine to form flakes or lentils. The flakes or lentils were passed through a comminuting machine (Fitzpatrick) to provide smaller pieces of lentils.

The caplets were molded using injection-molding technology. Methods of injection molding, the necessary equipment, and operating conditions are well known in the art. See, for example, U.S. Pat. Nos. 4,629,621, 4,744,976, 4,774,074, 4,806,337, and 5,082,655, which are incorporated by reference.

The method was carried out using an all electric, 50-ton model ACT-50 injection molding machine. The lentils were fed into the hopper of an injection molding machine (ACT 50-D Cincinnati Milacorn). The caplets were prepared using 0.68"×0.23" capsule shaped cold runner mold and cavity inserts. The barrel temperatures were set to a temperature range of 130–150° F. The shot size was set from 0.8 to 0.9 inch. The mold chillers were set to a temperature of 8–10° C.

The mold was then closed using semi-automatic mode and the selected mold cavities were filled with material flowing at 0.1 to 0.4 inch per second and at an injection pressure of 1000 to 1200 pounds per square inch. At the end of the 8 to 12 second injection time and the 1 to 3 second pack pressure of 100–500 pounds per square inch, the mold cooling time of 10 to 14 seconds allowed the extruder to return to the starting shot size position of 0.8 to 0.9 inch. The cooling timer timed out, allowing the mold to open 8 inches and the injection cycle pulses 2 to 4 times at a speed of 5 to 12 inches per second. At the same time the ejection cycle was operating, an air blast of 40 to 80 psi was directed at the spray to assure it was clear from the mold before starting the next cycle. After several cycles of running in the semi-automatic mode, with all caplet parts injecting into the collection bin, the automatic cycle mode could be activated. Cycle stability would be reached after running for approximately 5 minutes.

Example 2
Progesterone Oral Caplets, 200 mg

The composition for preparing progesterone oral caplets constituting 200 mg of progesterone per caplet is provided in Table 2 below.

TABLE 2

| Component | mg/caplet | % (by weight) |
| --- | --- | --- |
| Micronized progesterone | 200.00 | 51.55 |
| Polyethylene glycol 1450 | 38.80 | 10.00 |
| Polyethylene glycol 3350 | 131.74 | 33.95 |
| Polyethylene glycol 8000 | 15.52 | 4.00 |
| Titanium dioxide | 1.94 | 0.50 |
| TOTAL | 388.00mg | 100.00% |

Oral caplets constituting 200 mg of progesterone per caplet were prepared according to the process set forth in Example 1 except that during the injection molding process, mold cavities of 0.545"×0.240" were used.

Example 3
Progesterone Oral Caplets, 200 mg

The composition for preparing progesterone oral caplets constituting 200 mg of progesterone per caplet is provided in Table 3 below.

TABLE 3

| Component | mg/caplet | % (by weight) |
| --- | --- | --- |
| Micronized progesterone | 200.00 | 51.55 |
| Polyethylene glycol 1450 | 40.16 | 10.35 |
| Polyethylene glycol 3350 | 116.40 | 30.00 |
| Polyethylene glycol 8000 | 29.48 | 7.60 |
| Titanium dioxide | 1.94 | 0.50 |
| TOTAL | 388.00mg | 100.00% |

The procedure for preparing 200 mg progesterone oral caplets was as described above in Example 2.

Example 4
Progesterone Oral Caplets, 150 mg

The composition for preparing progesterone oral caplets constituting 150 mg of progesterone per caplet is provided in Table 4 below.

TABLE 4

| Component | mg/caplet | % (by weight) |
| --- | --- | --- |
| Micronized progesterone | 150.00 | 38.66 |
| Polyethylene glycol 1450 | 54.32 | 14.00 |
| Polyethylene glycol 3350 | 146.82 | 37.84 |
| Polyethylene glycol 8000 | 34.92 | 9.00 |
| Titanium dioxide | 1.94 | 0.50 |
| TOTAL | 388.00mg | 100.00% |

The procedure for preparing 150 mg progesterone oral caplets was as set forth in Example 2.

Example 5
Progesterone Oral Caplets, 150 mg

The composition for preparing progesterone oral caplets constituting 150 mg of progesterone per caplet is provided in Table 5 below.

TABLE 5

| Component | mg/caplet | % (by weight) |
|---|---|---|
| Micronized progesterone | 150.00 | 38.66 |
| Polyethylene glycol 1450 | 51.07 | 13.16 |
| Polyethylene glycol 3350 | 147.32 | 37.97 |
| Polyethylene glycol 8000 | 37.67 | 9.71 |
| Titanium dioxide | 1.94 | 0.50 |
| TOTAL | 388.00mg | 100.00% |

The procedure for preparing 150 mg progesterone oral caplets was as set forth in Example 2.

Example 6
Progesterone Oral Caplets, 75 mg

The composition for preparing progesterone oral caplets constituting 75 mg of progesterone per caplet is provided in Table 6 below.

TABLE 6

| Component | mg/caplet | % (by weight) |
|---|---|---|
| Micronized progesterone | 75.00 | 18.75 |
| Polyethylene glycol 1450 | 67.00 | 16.75 |
| Polyethylene glycol 3350 | 152.00 | 38.00 |
| Polyethylene glycol 8000 | 24.00 | 6.00 |
| Pregelatinized starch (Starch 1500) | 80.00 | 20.00 |
| Titanium dioxide | 2.00 | 0.50 |
| TOTAL | 400.00mg | 100.00% |

The procedure for preparing 75 mg progesterone oral caplets was as set forth in Example 2 except that Example 6 has pregelatinized starch as an additional ingredient.

Example 7
Progesterone Oral Caplets, 200 mg

The composition for preparing progesterone oral caplets constituting 200 mg of progesterone per caplet is provided in Table 7 below.

TABLE 7

| Component | mg/caplet | % (by weight) |
|---|---|---|
| Micronized progesterone | 200.00 | 43.10 |
| Polyethylene glycol 1450 | 56.60 | 12.20 |
| Polyethylene glycol 3350 | 163.30 | 35.20 |
| Polyethylene glycol 8000 | 41.80 | 9.00 |
| Titanium dioxide | 2.30 | 0.50 |
| TOTAL | 464.00mg | 100.00% |

The above-listed quantities of polyethylene glycol 1450, polyethylene glycol 3350 and polyethylene glycol 8000 were melted into an appropriate size heated kettle. The molten carrier was mixed for 5–10 minutes. Titanium dioxide was added through a size 20 mesh into the molten mixture and the mixture was stirred for additional 10 minutes. Micronized progesterone was dispersed into the kettle while mixing. After all the micronized progesterone has been added, stirring was continued for another 30 minutes. The material was then poured onto a sheet of aluminum foil and allowed to cool and harden. The hard sheet was then passed through screen #20. The milled material was encapsulated using size 0 capsules.

Example 8
Progesterone Oral Caplets, 100 mg

The composition for preparing progesterone oral caplets constituting 100 mg of progesterone per caplet is provided in Table 8 below.

TABLE 8

| Component | mg/caplet | % (by weight) |
|---|---|---|
| Micronized progesterone | 100.00 | 52.63 |
| Lactose monohydrate (Fast Flo #316), NF | 57.70 | 30.37 |
| Microcrystalline cellulose (Avicel PH102), NF | 17.10 | 9.00 |
| Croscarmellose sodium, (Ac-Di-Sol), NF | 5.70 | 3.00 |
| Sodium lauryl sulfate, NF | 3.80 | 2.00 |
| Povidone, NF | 3.80 | 2.00 |
| Colloidal silicon dioxide, NF | 0.60 | 0.30 |
| Magnesium stearate, NF | 1.30 | 0.70 |
| *Ethyl alcohol anhydrous (SD3A) | 21.00 | |
| TOTAL | 190.00mg | 100.00% |

*Ethyl alcohol anhydrous is evaporated during processing.

The required quantities of micronized progesterone, lactose monohydrate, croscarmellose sodium, sodium lauryl sulfate and microcrystalline cellulose were transferred into an appropriate size mixer and mixed for 10 minutes. Povidone was dissolved in ethyl alcohol while the powders were being mixed. The powders were granulated with the povidone solution and the mixing continued until a moist granular mass was formed. Additional ethyl alcohol was added if needed to reach granulation and point. The granulation was transferred to a tray dry oven and dried at 55° C. for 10 . 15 hrs or until loss on drying was not more than 2.0%. The dried granules were passed through a size 20 mesh screen together with colloidal silicon dioxide. Next, the milled granulation was lubricated by mixing with the required quantities of magnesium stearate in a suitable blender. The granulate was then compressed to 190 mg per tablet on a rotary tableting machine using ¼ inch flat faced beveled edge toolings. To make a 200 mg progesterone capsules, 2 tablets of progesterone 100 mg were filled into each size 0 hard shell gelatin capsules.

Example 9
Preparation of Estradiol Tablet, USP, 1 mg

The composition for preparing an estradiol tablet constituting 1 mg estradiol per tablet is provided in Table 9 below.

TABLE 9

| Component | mg/caplet | % (by weight) |
|---|---|---|
| Estradiol, micronized, USP | 1.03 | 1.290 |
| Anhydrous lactose, NF | 60.00 | 75.000 |
| Microcrystalline cellulose (Avicel PH102) | 16.00 | 20.000 |
| Polacrilin potassium, NF | 2.40 | 3.000 |
| Magnesium stearate, NF | 0.40 | 0.500 |
| D&C Red #30 (27%) aluminum lake | 0.06 | 0.075 |
| FD&C Blue #1 (13%) aluminum lake | 0.06 | 0.075 |
| D&C Yellow #10 (18%) aluminum lake | 0.04 | 0.050 |
| TOTAL | 80.00mg | 100.00% |

Partial quantity of anhydrous lactose (e.g., about 17%), the required quantities of D&C Red #30 (27%) aluminum lake, FD&C Blue #1 (13%) aluminum lake, D&C Yellow #10 (18%) aluminum lake were passed through a size 20 mesh screen. The required quantities of estradiol and the remaining quantities of anhydrous lactose were transferred into an appropriate size mixer and were mixed for 10 minutes. The required quantities of microcrystalline cellulose, polacriline potassium and the milled colored mixtures were added into the lactose/estradiol mixture and the composition was mixed for 10 minutes. The granulate was then lubricated by mixing with the required quantities of magnesium stearate in the same mixer. The granulate was then compressed to 80 mg per tablet using 7/32" round flat faced beveled edge tooling on a rotary tabletting machine. The thickness range of the tablets was 0.104" to 0.112" and hardness range of the tablets is 2–6 Kp.

Example 10
Bioavailability of Progesterone Caplet

A pilot, single-dose, two period, randomized crossover study was conducted in healthy post-menopausal women to determine the relative oral bioavailability of two progesterone products under fasting conditions. The methodology for conducting randomized crossover studies are well-known in the medical and pharmaceutical arts.

Figure 1B:
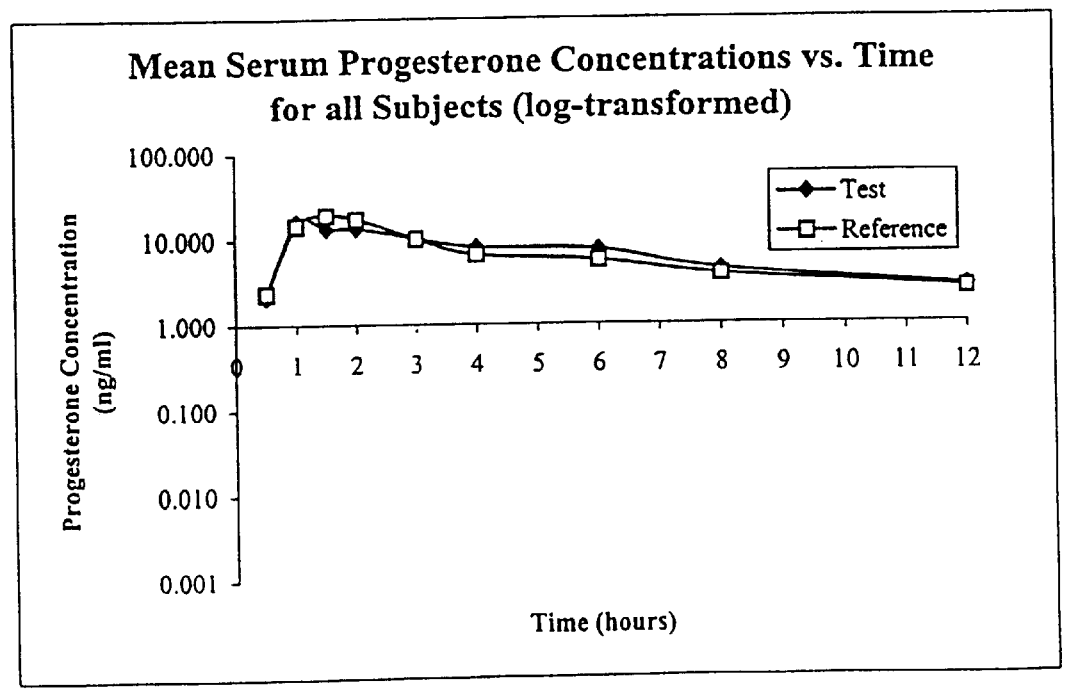
FIG. 1b displays the same data as in FIG. 1A, but on a logarithmic scale. The public should rely upon the more recent data previously mentioned that has been included in the prosecution history.

FIG. 1 shows the results of the experiment. In FIG. 1, "A" represents the data for a capsule formulation of progesterone 200 mg of the present invention (hereinafter referred to as Watson progesterone) and "B" represents the data for commercially available formulation, Prometrium® 100 mg (×2). The formulation is the same as in Example 1 except that the lentils were passed through a size 20 mesh and encapsulated in size 0 capsules.

FIG. 1 shows that the mean peak progesterone concentrations (Cmax) reached were 20.04±14.09 and 19.60±17.89 ng/ml following administration of the Watson progesterone and Prometrium® respectively. The means were not found to be statistically different as assessed by ANOVA (analysis of variance). The time to reach peak progesterone concentration (Tmax) was 2.31±1.71 hrs for the Watson progesterone and 1.44±0.32 hrs for Prometrium®. The means were not found to be statistically different at a p value of 0.05 or less. Area under the curve (AUC) (0-t) following administration of the Watson progesterone and Prometrium® were not found to be statistically different as assessed by ANOVA (analysis of variance). AUC (0-t) or the area under the drug concentration versus time curve, from time zero to the last measured concentration (12 hours), was calculated by the linear trapezoidal method.

This study showed that there were no statistically significant differences in the mean peak progesterone concentration (Cmax), mean time to reach peak progesterone concentration (Tmax), and Area under the curve (AUC) between the Watson solid oral progesterone formulation and the FDA approved oil based oral progesterone formulation, Prometrium®, following a single administration to healthy postmenopausal women.

Example 11
Bioavailability of Progesterone Caplet when Administered with Estradiol A pilot single dose, three period, randomized crossover study was conducted in 12 healthy postmenopausal women to determine the relative oral bioavailability of two progesterone products under fasted conditions. The study involved administration of a single progesterone caplet (300 mg), a single estradiol tablet (1 mg) or a combination of the estradiol tablet and the progesterone caplet.

The progesterone caplet resulted in a Cmax of 75.78±5.3 ng/mL of plasma progesterone, with a Tmax of 2.62±1.5 hours and an $AUC_{(0-24)}$ of 211.1±127 ng.hr/ml. The normalized Cmax is 0.25 ng/mL and the normalized AUC is 0.7 ng.hr/ml/mg. The normalized data was obtained by dividing the corresponding data with the dose.

The combination capsule resulted in a Cmax of 122.98+/−157.9 ng/mL of plasma progesterone with a Tmax of 1.88+/− 0.98 hours and an $AUC_{(0-24)}$ of 276.6+/−251.4 ng.hr/ml. The normalized Cmax is 0.41 ng/mL and the normalized AUC $_{(0-24)}$ is 0.9 ng.hr/ml/mg.

The above data indicate that the normalized Cmax of progesterone from the combination capsule (0.41 ng/ml) is about 60% higher than the normalized Cmax for the progesterone-only caplet (0.25 ng/ml). Similarly, the normalized AUC for progesterone from the combination capsule (0.9 ng.hr/ml/mg) is about 30% higher than the AUC for progesterone from the progesterone-only caplet (0.7 ng.hr/ml/mg). These are surprising results and suggest that higher Cmax and AUC levels of progesterone can be achieved by providing progesterone in a solid oral dosage form having a solid polymeric carrier and in combination with an estrogen.

Examples 10 and 11 were included in the application as filed. Subsequent to the filing of the application, the assignee has been involved in testing for regulatory approval which provides more recent and hence more definitive data. All tests as reported in the application as filed are retained only to provide information then available. The new information upon which the applicants rely for regulatory approval is being included in the prosecution history of the patent file.

We claim:

1. In an oral dosage form suitable to deliver a combined dosage of progesterone and an estrogen via the gastrointestinal tract, the improvement which upon oral administration provides a blood concentration of from about 0.1 ng/ml to about 400 ng/ml progesterone and comprises a combination that includes (a) a first solid form containing from about 25 mg to about 500 mg micronized progesterone, said first solid form having been derived from the extrusion of a polymer matrix extruded from a mixture comprising micronized progesterone in a solid polyethylene glycol carrier which is a mixture of at least 10% by weight polyethylene glycol 1450, at least 30% by weight polyethylene glycol 3350 and at least 4% by weight polyethylene glycol 8000, the micronized progesterone having first been dispersed in molten polyethylene gylcol and, after cooling to a solid form, having been extruded, said mixture constituting from about 45% to about 65% weight of said first solid form; and (b) a second solid form which contains from about 0.25 mg to about 5 mg of estradiol.

2. An oral dosage form according to claim 1, wherein said first solid form comprises from about 0.1 to about 5.0% by weight of sodium lauryl sulfate.

3. An oral dosage form according to claim 1, wherein said first solid form comprises from about 0.1 to about 5.0% by weight of glyceryl monooleate.

4. An oral dosage form according to claim 1, wherein said first solid form comprises from about 0.1 to about 5.0% by weight of sorbitan ester.

5. An oral dosage form according to claim 1, wherein said first solid form comprises from about 0.1 to about 5.0% by weight of docusate sodium.

6. An oral dosage form according to claim 1, wherein said first solid form comprises from about 0.1 to about 5.0% by weight of cetrimide.

7. An oral dosage form according to claim 1, wherein said first solid form is a caplet and said second solid form is a tablet.

8. A method of providing an oral dosage of a combination therapy of progesterone and estradiol which comprises administering to a patient an oral dosage form suitable to deliver a combined dosage of progesterone and an estrogen via the gastrointestinal tract which upon oral administration provides a blood concentration of from about 0.1 ng/ml to about 400 ng/ml progesterone; said dosage form comprising a combination that includes (a) a first solid form containing from about 25 mg to about 500 mg micronized progesterone, said first solid form having been derived from the extrusion of a polymer matrix extruded from a mixture comprising micronized progesterone in a solid polyethylene glycol carrier which is a mixture of at least 10% by weight polyethylene glycol 1450, at least 30% by weight polyethylene glycol 3350 and at least 4% by weight polyethylene glycol 8000, the micronized progesterone having first been dispersed in molten polyethylene glycol and, after cooling to a solid form, having been extruded, said mixture constituting from about 45% to about 65% weight of said first solid form; and (b) a second solid form which contains from about 0.25 mg to about 5 mg of estradiol.

* * * * *